United States Patent
Beumer et al.

(10) Patent No.: US 9,249,074 B2
(45) Date of Patent: Feb. 2, 2016

(54) SYNTHESIS OF TETRAHYDROMYRCENOL

(71) Applicant: DSM IP ASSETS B.V., Heerlen (NL)

(72) Inventors: Raphael Beumer, Basel (CH); Werner Bonrath, Basel (CH); Jonathan Alan Medlock, Basel (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 14/647,636

(22) PCT Filed: Nov. 28, 2013

(86) PCT No.: PCT/EP2013/075003
§ 371 (c)(1),
(2) Date: May 27, 2015

(87) PCT Pub. No.: WO2014/083121
PCT Pub. Date: Jun. 5, 2014

(65) Prior Publication Data
US 2015/0329451 A1    Nov. 19, 2015

(30) Foreign Application Priority Data

Nov. 28, 2012  (EP) .................................. 12194596

(51) Int. Cl.
*C07C 29/10*     (2006.01)
*C07C 29/17*     (2006.01)

(52) U.S. Cl.
CPC ............... *C07C 29/172* (2013.01); *C07C 29/10* (2013.01); *C07C 29/103* (2013.01)

(58) Field of Classification Search
CPC ............................ C07C 29/10; C07C 29/103
USPC ........................................................ 568/907
See application file for complete search history.

(56) References Cited

FOREIGN PATENT DOCUMENTS

DE         11 18 190        11/1961

OTHER PUBLICATIONS

International Search Report for PCT/EP2013/075003 mailed Jan. 20, 2014, three pages.
Y. Hitomi et al., "An Iron (III)-Monoamidate Complex Catalyst for Selective Hydroxylation of Alkane C H Bonds with Hydrogen Peroxide", *Angewandte Chemie International Edition*, vol. 51, No. 14, Apr. 2, 2012, pp. 3448-3452.
L. Gomez et al., "Stereospecific C—H Oxidation with H2O2 Catalyzed by a Chemically Robust Site-Isolated Iron Catalyst", *Angewandte Chemie International Edition*, vol. 48, No. 31, Jul. 20, 2009, pp. 5720-5723.

*Primary Examiner* — Elvis O Price
(74) *Attorney, Agent, or Firm* — Nixon & Vanderhye P.C.

(57) ABSTRACT

The present invention relates to a new and improved synthesis of tetrahydromyrcenol (IUPAC name: 2,6-dimethyl-2-octanol).

7 Claims, No Drawings

SYNTHESIS OF TETRAHYDROMYRCENOL

This application is the U.S. national phase of International Application No. PCT/EP2013/075003 filed 28 Nov. 2013 which designated the U.S. and claims priority to EP 12194596.8 filed 28 Nov. 2012, the entire contents of each of which are hereby incorporated by reference.

The present invention relates to a new and improved synthesis of tetrahydromyrcenol (IUPAC name: 2,6-dimethyl-2-octanol).

Tetrahydromyrcenol (CAS Number: 18479-57-7), which is the following compound of formula (I)

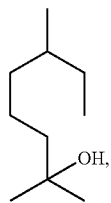

(I)

is a well-known compound in the flavour and fragrance industry. It used widely for many applications. It is described olfactory as "fresh, overall citrus-floral and sweet odour with terpenic undertones".

Due to the importance of tetrahydromyrcenol, there is always a need for an improved process for its production.

We found that that the reductive ring opening of a compound of formula (II)

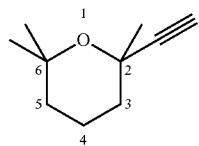

(II)

results in an excellent selectivity and yield of tetrahydromyrcenol.

It is surprising that the reductive ring opening does not result (or only in minimal amounts) in undesired side products such as i.e.

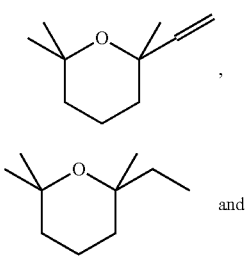

(III)

(IV)

and

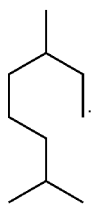

(V)

Furthermore it is surprising that the ring opens selectively at the "correct" position (position 2; which leads to tetrahydromyrcenol) and not at position 6. Such a ring opening would lead (for example) to a compound of formula (VI)

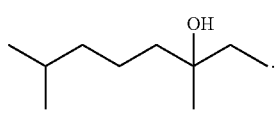

(VI)

Compound of formula (VI) is not found in the reaction mixture at the end of the synthesis, as well as other possible reaction products from such ring opening are not found.

Therefore the present invention relates to a process for production of compound of formula (I)

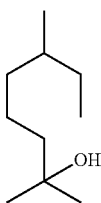

(I)

by a reductive ring-opening of a compound of formula (II)

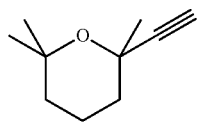

(II)

The compound of formula (II) can, for example, be prepared from dehydrolinalool by ring closure catalysed by tungsten, molybdenum or polyphosphoric acid (Strickler et al., Helv. Chem. Acta 1966, 49, 2055; Erman et al., Tetrahedron 1976, 34, 2981, and Belgian Patent No. 852 918).

The reduction agent used in the process according to the present invention is preferably $H_2$ gas.

Therefore the process according to the present invention is preferably carried out under pressure.

Usually the pressure is at least 1 bar, preferably at least 3 bars.

A preferred range for the pressure under which the process according to the present invention is carried out, is 1-20 bar, more preferably 3-15 bar.

All the pressures given in the context of the present patent application are always absolute pressures.

Therefore the present invention relates to a process for production of compound of formula (I) by a reductive ring-opening of a compound of formula (II), characterized in that the reaction is carried out with H$_2$-gas at a pressure of 1-20 bar, preferably at 3-15 bar.

The process according to the present invention is usually carried out at temperatures from 15-100° C., preferably from 20-80° C.

Therefore the present invention relates to a process for production of compound of formula (I) by a reductive ring-opening of a compound of formula (II), characterized in that the reaction is carried out at temperatures from 15-100° C., preferably from 20-80° C.

Preferably the present invention relates to a process for production of compound of formula (I) by a reductive ring-opening of a compound of formula (II), characterized in that the reaction is carried out with H$_2$-gas at a pressure of 1-20 bar, preferably at 3-15 bar and at temperatures from 15-100° C., preferably from 20-80° C.

The process according to the present invention can be carried out with or without a solvent.

Preferably the process according to the present invention is carried out in an inert solvent (or a mixture of solvents). Inert solvent means that the solvent will not take part in the reaction process.

The solvent must be liquid at the reaction condition used in a process according to the present invention.

Suitable solvents are i.e. alcohols (such methanol, ethanol), hydrocarbons (such as n-hexane, n-heptane), esters, ethers (such as THF), chlorinated hydrocarbons (such as CH$_2$Cl$_2$).

Therefore the present invention relates to a process for production of compound of formula (I) by a reductive ring-opening of a compound of formula (II), characterized in that the reaction is carried out in a solvent or in a mixture of solvents (preferably alcohols, hydrocarbons, esters, ethers and chlorinated hydrocarbons).

Preferably the present invention relates to a process for production of compound of formula (I) by a reductive ring-opening of a compound of formula (II), characterized in that the reaction is carried out
with H$_2$-gas at a pressure of 1-20 bar, preferably at 3-15 bar and
at temperatures from 15-100° C., preferably from 20-80° C. and a solvent or in a mixture of solvents (preferably alcohols, hydrocarbons, esters, ethers and chlorinated hydrocarbons).

Preferably the process according to the present invention is carried out in the presence of a catalyst.

The catalyst is a transition metal on a support material. Usually the support material is carbon or a solid acid. Preferred transition metals are Pt, Rh and Pd, More preferred is palladium on carbon (Pd/C). Such a catalyst (CAS number of 7440-05-3) is commercially available for example from Sigma Aldrich.

Therefore the present invention relates to a process for production of compound of formula (I) by a reductive ring-opening of a compound of formula (II), characterized in that the reaction is carried out is carried out in the presence of a catalyst (preferably a transition metal on a support material, more preferably Pd/C).

Preferably the catalyst is present in the process in amount of up to 10 wt-% (based on the weight of compound of formula (II)), more preferably up to 5 wt %.

Preferably the present invention relates to a process for production of compound of formula (I) by a reductive ring-opening of a compound of formula (II), characterized in that the reaction is carried out
with H$_2$-gas at a pressure of 1-20 bar, preferably at 3-15 bar, and
at temperatures from 15-100° C., preferably from 20-80° C., and
a solvent or in a mixture of solvents (preferably alcohols, hydrocarbons, esters, ethers and chlorinated hydrocarbons), and
in the presence of up to 10 wt-% (based on the total weight of compound of formula (II)) of at least one catalyst (preferably a transition metal on a support material, more preferably Pd/C), preferably up to 5 wt %.

The process according to the present invention is usually carried out in the presence of an acid. The acid can be organic as well as inorganic (as well as mixtures).

Suitable acids are i.e. HCl, H$_2$SO$_4$, p-toluenesulfonic acid. It is also possible to use solid acids.

Preferably the acid is present in an amount of 1-20 wt-% (based on the total weight of compound of formula (II))

Therefore the present invention relates to a process for production of compound of formula (I) by a reductive ring-opening of a compound of formula (II), characterized in that the reaction is carried out is carried out in the presence of an organic and/or an inorganic acid, as well as mixtures thereof (preferably HCl, H$_2$SO$_4$, p-toluenesulfonic acid).

Preferably the present invention relates to a process for production of compound of formula (I) by a reductive ring-opening of a compound of formula (II), characterized in that the reaction is carried out
with H$_2$-gas at a pressure of 3-20 bar, preferably at 3-15 bar, and
at temperatures from 15-100° C., preferably from 20-80° C., and
a solvent or in a mixture of solvents (preferably alcohols, hydrocarbons, esters, ethers and chlorinated hydrocarbons), and
in the presence of a catalyst (preferably a transition metal on a support material, more preferably Pd/C), and
in the presence of an organic and/or an inorganic acid, as well as mixtures thereof (preferably HCl, H$_2$SO$_4$, p-toluenesulfonic acid).

The following examples illustrate the present invention.

All the parts and percentages in the Examples are related to the weight (when not otherwise stated) and the temperature is given in ° C. (when not otherwise stated).

EXAMPLES

Example 1

8 mg of the catalyst (Pd/C) was added to a 8 ml glass reactor and 2-ethynyl-2,6,6-trimethyl-tetrahydropyran (210 mg, 95%) was added. Heptane (1.5 g) and concentrated hydrochloric acid (10 µl) were added and the reactor was sealed. The reactor was purged with argon 3 times (by pressurising to 5 bar followed by release of the pressure) and 3 times with hydrogen (pressurise to 5 bar then release). The reaction mixture was heated to 50° C., pressurised to 10 bar hydrogen and stirred until no more hydrogen consumption was observed and then for a further 30-60 minutes. The stirring was stopped and the reaction allowed to cool to room temperature.

The pressure was released and the reactor purged 2 times with argon. After filtration to remove the catalyst, the reaction mixture was analysed by GC to determine conversion and selectivity.

The selectivity and the yield was more than 90%.

The examples in the following table have been synthesised in analogy to example 1. The amount of catalyst, the acid, the amount of acid, the pressure and the reaction temperature have been varied.

TABLE 1

| Exp. | Solvent | Amount Cat [mg] | Acid | Amount acid | p [bar] | T [° C.] | Yield [%] |
|---|---|---|---|---|---|---|---|
| 2 | THF | 14 | HCl | 10 µl | 10 | 50 | 68 |
| 3 | n-heptane | 17 | HCl | 10 µl | 10 | 50 | 78 |
| 4 | n-heptane | 23 | HCl | 10 µl | 10 | 30 | 78 |
| 5 | n-heptane | 26 | HCl | 10 µl | 3 | 50 | 74 |
| 6 | n-heptane | 9 | HCl | 10 µl | 3 | 70 | 87 |
| 7 | n-heptane | 10 | p-toluene-sulfonic acid | 11 mg | 10 | 50 | 50 |

The yield and the selectivity are identical due to the fact that the conversion is 100%.

The invention claimed is:

1. A process for production of compound of formula (I)

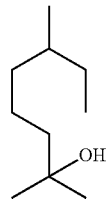

(I)

by a reductive ring-opening of a compound of formula (II)

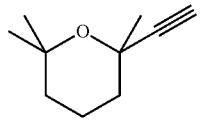

(II)

2. Process according to claim 1, wherein the reducing agent is $H_2$ gas.

3. Process according to claim 2, wherein process is carried out under pressure of at least 1 bar.

4. Process according to claim 1, wherein the process is carried out at temperatures from 15-100° C.

5. Process according to claim 1, wherein the process is carried out with or without a solvent.

6. Process according to claim 1, wherein the process is carried out in the presence of a catalyst.

7. Process according to claim 1, wherein the process is carried out in the presence of an acid.

* * * * *